US00PP36662P2

(12) United States Plant Patent
Gómez Porras et al.

(10) Patent No.: US PP36,662 P2
(45) Date of Patent: May 13, 2025

(54) OLIVE TREE NAMED 'I 24'

(50) Latin Name: *Olea europaea*
Varietal Denomination: I 24

(71) Applicant: TODOLIVO S.L., Cordova (ES)

(72) Inventors: Jose María Gómez Porras, Cordova (ES); Luis Rallo Romero, Cordova (ES); Diego Barranco Navero, Cordova (ES); Concepción Muñoz Díez, Cordova (ES); Carlos Trapero Ramírez, Cordova (ES); Pedro Valverde Caballero, Cordova (ES)

(73) Assignee: Todolivo S.L., Cordova (ES)

( * ) Notice: Subject to any disclaimer, the term of this patent is extended or adjusted under 35 U.S.C. 154(b) by 0 days.

(21) Appl. No.: 18/445,927

(22) Filed: Mar. 27, 2024

(51) Int. Cl.
*A01H 5/08* (2018.01)
*A01H 6/00* (2018.01)

(52) U.S. Cl.
USPC ..... Plt./158
CPC ..... *A01H 6/00* (2018.05)

(58) Field of Classification Search
USPC ..... Plt./156, 158
See application file for complete search history.

*Primary Examiner* — Karen M Redden
(74) *Attorney, Agent, or Firm* — Hunt IP Law

(57) ABSTRACT

The new and distinct variety of olive tree variety 'I 24' is provided. The variety can be distinguished by its outstanding features of low vigor, high yield, and high oil production.

5 Drawing Sheets

Latin name of the genus and species:

Botanical classification: a. Genus—*Olea*. b. Species—*europaea*.

Variety denomination: The new olive tree claimed is of the variety denominated 'I 24'.

CROSS REFERENCE TO RELATED APPLICATIONS

None.

BACKGROUND OF THE INVENTION

Field of the Invention

The present invention relates to a new and distinct variety of olive tree, which has been given the variety denomination of 'I 24'.

Background of the Related Art

Olive oil continues to increase in popularity. Accordingly, there is a continuing need to develop new and improved olive oils to meet the increased demand for use in various food types and in cooking. Many olive varieties are self-sterile. As a result, there is a need for the development of new olive varieties which are self-pollination and produce a high yield of new and improved olive oil for commercialization.

SUMMARY OF THE INVENTION

The present invention relates to a new and distinct variety of olive tree, which has been given the variety denomination of 'I 24'. 'I 24' is intended for use for oil production.

The new olive tree variety is a selection resulting from a sexual cross of olive trees at Córdoba, Spain in 2008, involving a seed parent known as 'Arbosana' (unpatented) and a pollen parent known as 'Koroneiki' (unpatented).

The selection was subsequently evaluated 10 years at Córdoba, Spain.

Asexual reproduction of the new variety by cutting propagation since 2008 at Córdoba, Spain has demonstrated that the new variety reproduces true to type with all of the morphological characteristics, as herein described, firmly fixed and retained through successive generations of such asexual propagation.

Selection criteria were low vigor, high yield, and high oil production.

Plants of the new variety stand out for its high production compared to its parents 'Arbosana' and 'Koroneiki'. Additionally, this variety is notable for its low vigor. This variety produces fruit with medium weight which are colored black at full maturity. The new variety differs from its parents in oil production, with an average 5-10 higher than that of its parents. The new variety is 3-5% less vigorous than 'Arbosana' and 10-15% less vigorous than 'Koroneiki'.

Plants of the new variety differ from the varieties mentioned in co-pending application Ser. No. 18/445,919 (for Olive Tree Variety Named 'I 72'), Ser. No. 18/445,923 (for Olive Tree Variety Named 'I-73'), and Ser. No. 18/445,920 (for Olive Tree Variety Named 'I 74'). The new variety differs from 'I 72' and 'I 73' mainly in its parents. The parents of 'I 72' are 'Koroneiki' x 'Arbosana' and those of 'I 73' are 'Arbequina' x 'Picual'. The new variety also differs from 'I 72', 'I 73', and 'I 74' in its growth habit, which is more compact; and in its vigor, which is less vigorous than these varieties. There are also differences in leaf and fruit morphology.

Compared to the 'Arbequina' variety, which is a well-known and popular olive variety in the industry, the new variety has a higher olive production and a lower vigor. The growth habit of 'I 24' is hanging or weeping, while the growth habit of 'Arbequina' is open. The color of the fruit at full maturity of 'I 24' is dark violet, while that of the 'Arbequina' variety is black. 'I 24' produces 4-8% more olive oil and is 10-15% less vigorous than 'Arbequina'.

BRIEF DESCRIPTION OF THE DRAWINGS

The accompanying photographic illustrations show the typical appearance of the new variety 'I 24'. The colors are as nearly true as is reasonably possible in a color representation of this type. Colors in the photographs may differ slightly from the color values cited in the detailed botanical description which accurately describes the colors of the new plant.

DETAILED BOTANICAL DESCRIPTION

Figure 1:
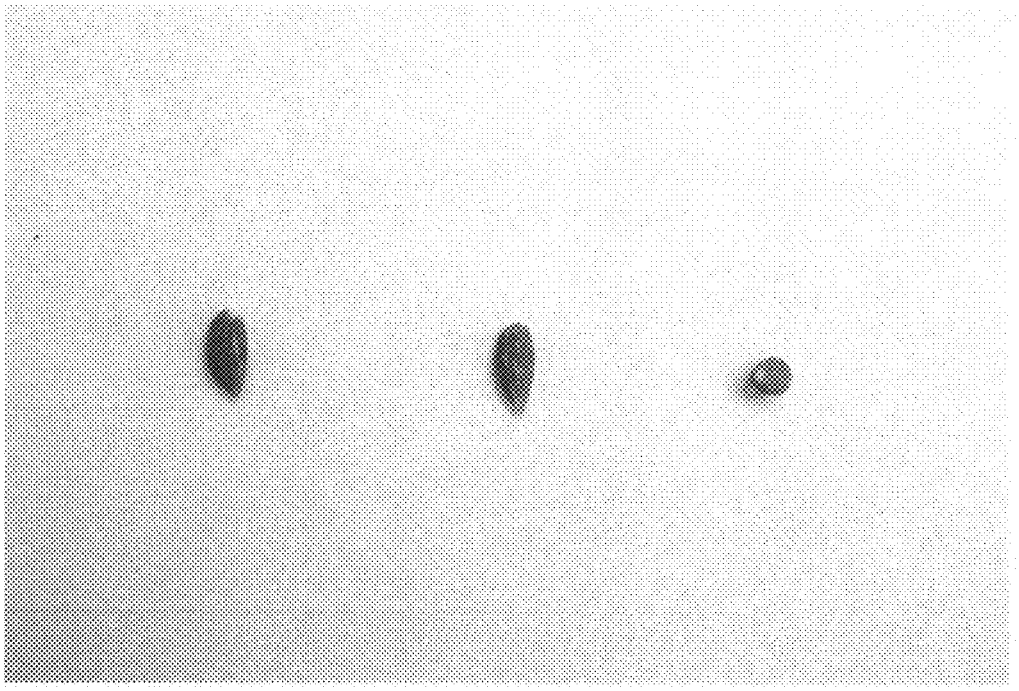
FIG. 1 is a photograph of the new variety 'I 24', demonstrating stones.
Figure 2:
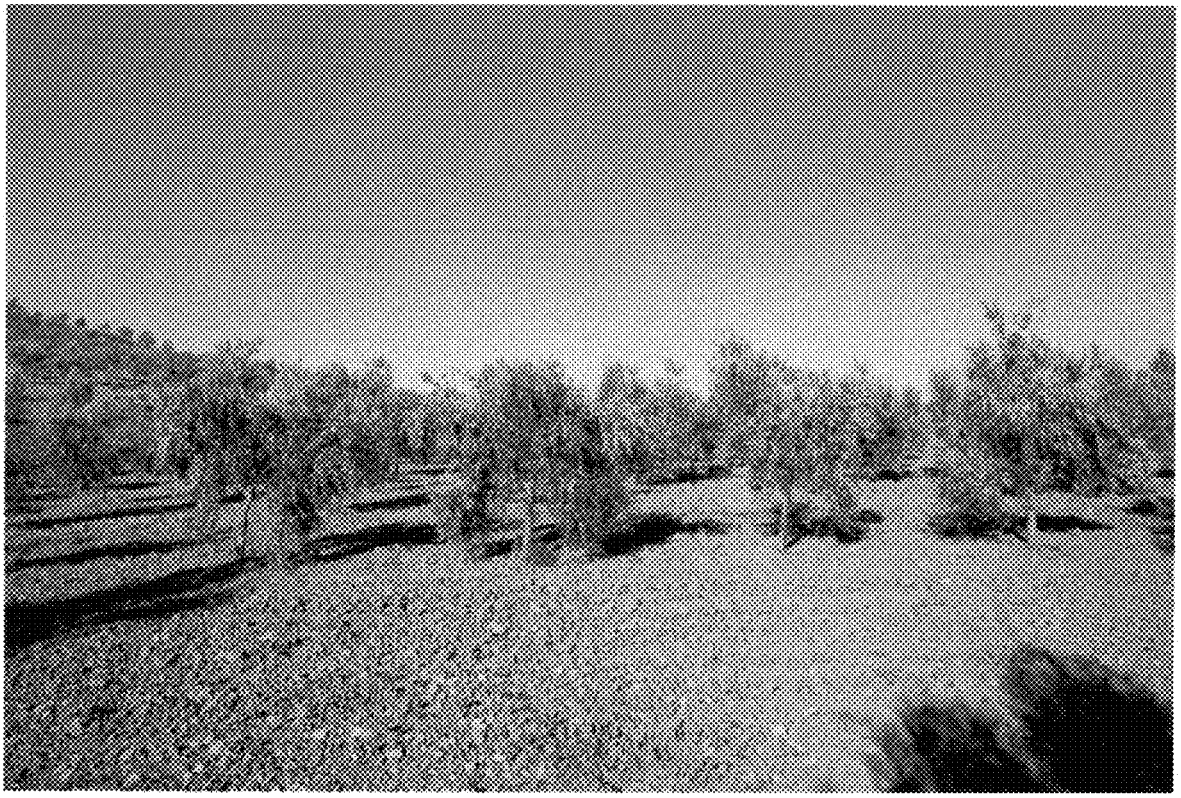
FIG. 2 is a photograph of the new variety 'I 24', demonstrating the behavior of the variety when grown in a hedge line.
Figure 3:
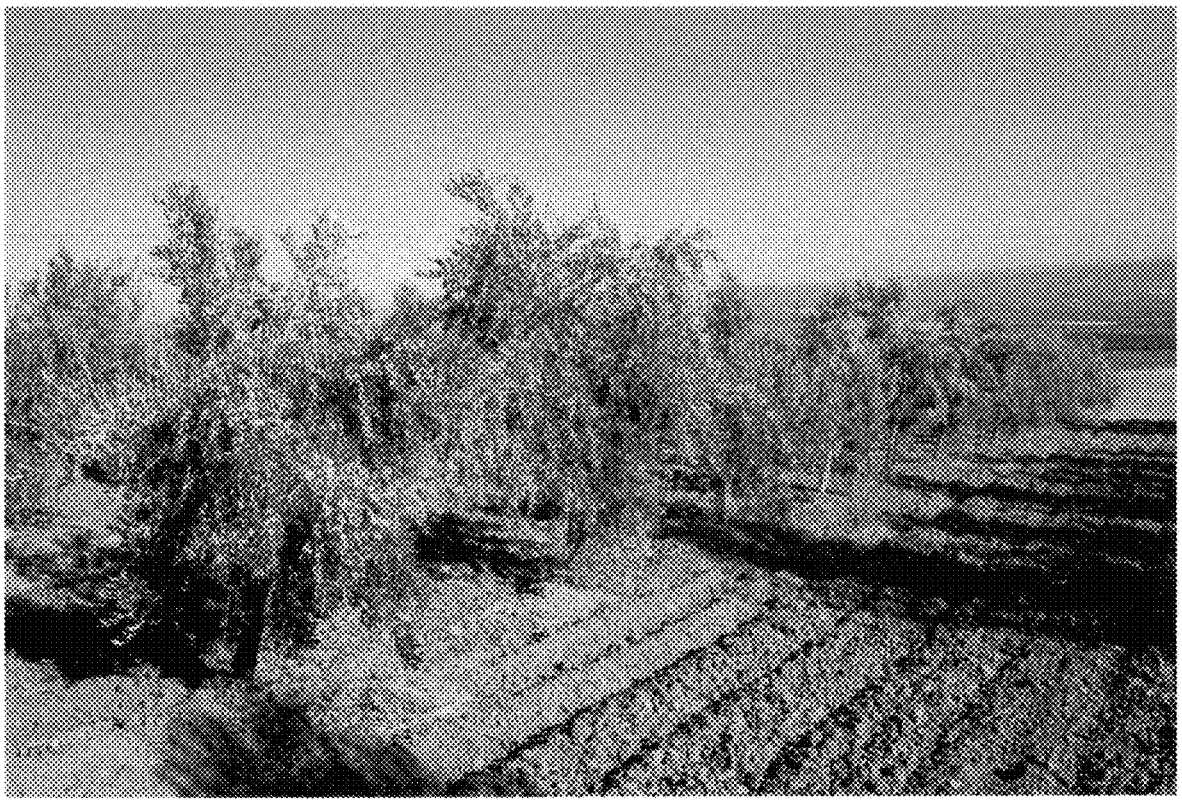
FIG. 3 is a photograph of the new variety 'I 24', demonstrating behavior when grown in a hedge line.
Figure 4:
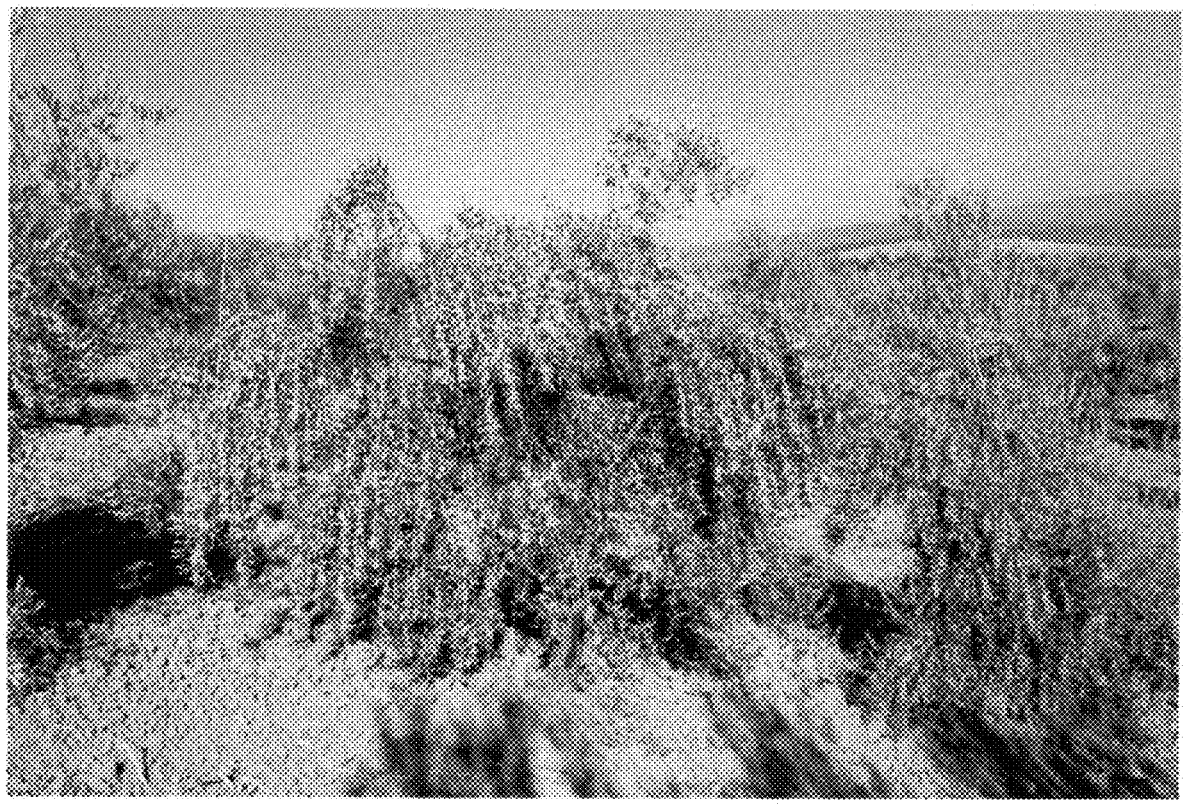
FIG. 4 is a photograph of the new variety 'I 24', demonstrating fruit load.
Figure 5:
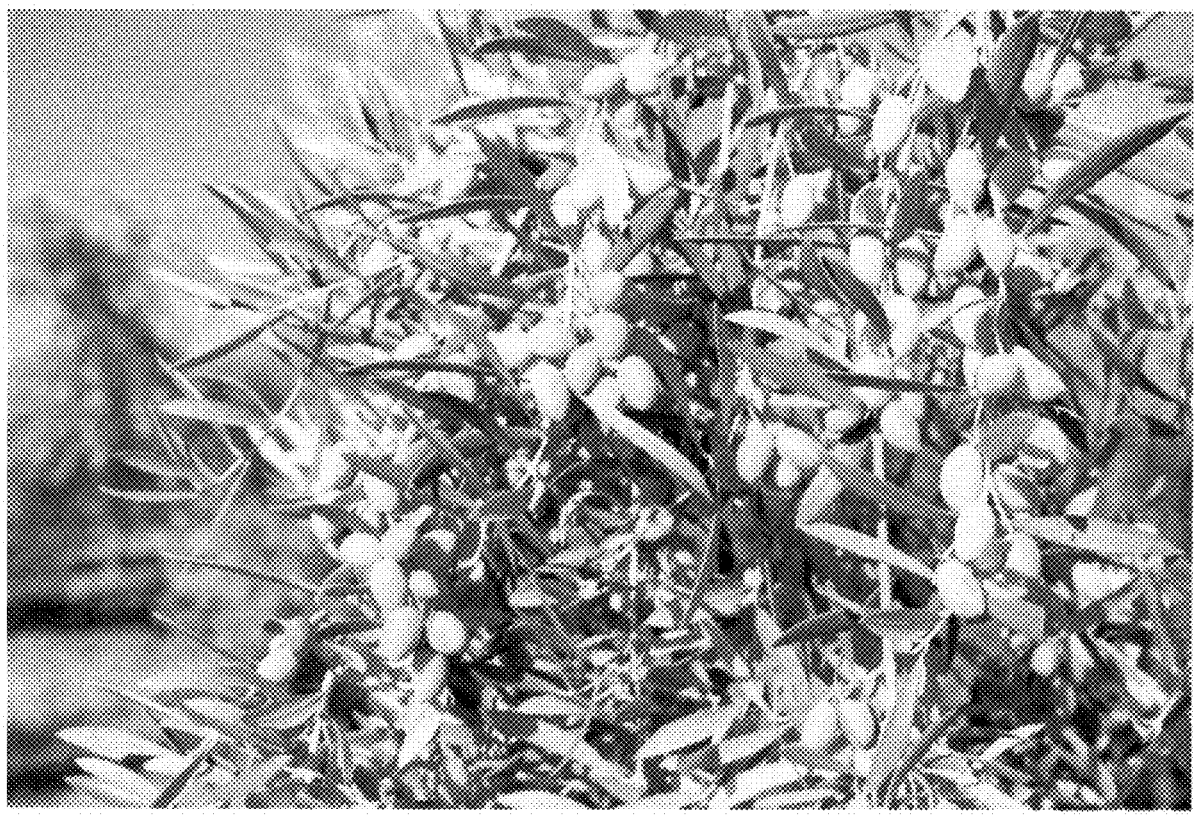
FIG. 5 is a photograph of the new variety 'I 24', demonstrating fruit, fruit color, and branching habit.

The following detailed description sets forth the distinctive characteristics of 'I 24'. The datum which defines these characteristics was collected from asexual reproductions of the original selection. Dimensions, sizes, colors, and other characteristics are approximations and averages set forth as accurately as possible. The plant history was taken on plants approximately 5 years and 8 months of age, and the descriptions relate to plants grown in Córdoba, Spain. Color notations are in reference to the standard Color Chart is that of The Royal Horticultural Society (R.H.S. Colour Chart, 2015 edition. London, England).

Classification:

a. *Latin name.*—*Olea europaea* L.
b. *Common name.*—Olive tree.
c. *Variety name.*—'I 24'.

Parentage:

a. *Female parent.*—'Arbosana' (unpatented).
b. *Male parent.*—'Koroneiki' (unpatented).

PLANT

General:

a. *Height.*—240 cm (average).
b. *Width.*—160 cm (average).
c. *Growth habit.*—Drooping.
d. *Vigor.*—Low-medium.

ROOTS

General:

e. *Rooting habit.*—Normal-Dense
f. *Texture.*—Fibrous.
g. *Color designation* (*young roots*).—155A.
h. *Color designation* (*old roots*).—157A.

STEMS

General:

i. *Branching habit.*—Spreading.
j. *Trunk.*—i. Circumference — 10 cm. ii. Surface texture — Smooth. iii. Color — 199A.
k. *Main stems.*—i. Quantity — Dependent on the management and pruning. ii. Aspect — Smooth. iii. Strength — Robust. iv. Cross-section — Rounded Small. v. Circumference — 6 cm (diameter) at 50 cm above the soil. vi. Surface texture (young stems) — Smooth. vii. Surface texture (mature stems) — Smooth with lenticels. viii. Color designation (young stems) — 157A. ix. Color designation (mature stems) — 157B. x. Lenticels — Many, 1 mm long, 0.5 mm wide. xi. Internode length — Ranging from 5-12 cm.
l. *Lateral branches.*—i. Quantity — Abundant. ii. Cross-section — Oval. iii. Length — 80-180 cm iv. Internode length — Ranging from 2-3 cm. v. Texture — Smooth with raised lenticels. vi. Aspect — Outward. vii. Strength — Flexible. viii. Color (young lateral branches) — 196D. ix. Color (mature lateral branches) — 197D. x. Pubescence — None.

FOLIAGE

General:

m. *Arrangement.*—Opposite.
n. *Attachment.*—Petiolate.
o. *Division.*—Simple. i. Length — Average 50 mm. ii. Width — Average 10 mm. iii. Thickness — 1.5-2 mm. iv. Shape — Acuminate. v. Aspect — Cuneate. vi. Apex — Acuminate. vii. Base — Cuneate. viii. Margin — Entire (smooth). ix. Texture of upper surface — Smooth. x. Texture of lower surface — Slightly pubescent. xi. Color of young lamina (upper surface) — 141B. xii. Color of young lamina (lower surface) — 142B. xiii. Color of mature lamina (upper surface) — 143B. xiv. Color of mature lamina (lower surface) — 142B. xv. Venation pattern — Pinnate.
p. *Petiole.*—i. Length — 2 mm. ii. Diameter — 1.2 mm. iii. Texture — Smooth. iv. Strength — Medium. v. Color — 142B.

INFLORESCENCE

General:

q. *Type.*—Panicle.
r. *Natural flowering season.*—Spring.
s. *Flowering habit.*—1-10 days during May.
t. *Length.*—2.5-6.5 cm.
u. *Width.*—1-3 cm.
v. *Quantity of florets per inflorescence.*—20-25.
w. *Peduncle.*—i. Length — 2.5-6.5 cm. ii. Width — 1.2 cm. iii. Texture — Smooth. iv. Strength — Medium. v. Color — 141D. vi. Diameter — 1.2 cm.
x. *Pedicels.*—i. Length — 2 mm. ii. Width — 1 mm. iii. Texture — Smooth. iv. Strength — Medium. v. Color — 141D.

FLOWER BUD

General:

y. *Shape*.—Globular.

z. *Length*.—2-4 mm.

aa. *Width*.—2 mm.

bb. *Color*.—157A.

FLOWER

General:

cc. *Type*.—Perfect.

dd. *Shape*.—Cruciform.

ee. *Persistence*.—Medium.

ff. *Fragrance*.—Smooth and intoxicating.

gg. *Diameter*.—3-6 mm.

hh. *Height*.—2-3 mm.

ii. *Calyx*.—i. Quantity of sepals — 4. ii. Arrangement — Rotate. iii. Diameter — 1 cm.

jj. *Sepals*.—i. Sepal fusion — Fused. ii. Length — 1 mm. iii. Width — 1 mm. iv. Shape — Bell shape. v. Apex — Obtuse. vi. Base — Cuneate. vii. Margin — Entire. viii. Texture — Smooth. ix. Color (upper surface) — 184A1. x. Color (lower surface) — 184A1.

kk. *Petals*.—i. Arrangement — Rotate. ii. Quantity — 4. iii. Fusion — Sympetalous petals fused at the proximal half of the corolla. iv. Shape — Acute. v. Apex — Acute. vi. Base — Cuneate. vii. Margin — Entire. viii. Texture — Smooth. ix. Color when opening (upper surface) — NN155D. x. Color when opening (lower surface) — NN155D. xi. Color when fully opened (upper surface) — NN155D. xii. Color when fully opened (lower surface) — NN155D. xiii. Color fading — None.

REPRODUCTIVE ORGANS

General:

ll. *Androecium*.—i. Stamen quantity — 2. ii. Filament length — Approximately 0.75 mm. iii. Filament color — 17D1. iv. Anther attachment — Basifixed. v. Anther shape — Hemispherical. vi. Anther size — 1 mm. vii. Anther color — 2A. viii. Abundance of pollen — Abundant. ix. Pollen color — 2A.

mm. *Gynoecium*.—i. Pistil quantity — 1. ii. Stigma shape — Bifid cone shape. iii. Stigma length — Approximately 0.75 mm. iv. Stigma color — 145D. v. Style size — Approximately 0.75 mm. vi. Style color — 145D. vii. Ovary position — Superior. viii. Ovary shape — Round. ix. Ovary diameter — Approximately 0.75 mm. x. Ovary color — 145D.

SEED AND FRUIT

General:

nn. *Fruit*.—i. Date of maturity — November-December. ii. Size — Medium. iii. Weight — 1.69 g (medium). iv. Diameter — 14.5 mm (medium). v. Length — 18 mm (medium). vi. Form — Ovoidal. vii. Suture — None. viii. Stem cavity — Medium. ix. Stem — Medium. x. Caliper — Medium. xi. Apex — Slightly. xii. Pistil point — Absent. xiii. Skin thickness — Less than 1 mm. xiv. Skin texture — Smooth. xv. Skin tendency to crack — None. xvi. Skin color — 83A xvii. Flesh color — 158C. xviii. Pit color — 144C. xix. Oil/juice production — 1,690 grams/plant in irrigation and 1,035 grams/plant in rain-fed systems. xx. Flavor — Different/Excellent. xxi. Ripening — Medium.

oo. *Stone*.—i. Quantity — 1. ii. Shape — Ovate. iii. Type — Slightly asymmetric. iv. Fibers — None. v. Weight — 0.29 g (medium). vi. Length — 14 mm (medium). vii. Width — 8 mm (medium). viii. Thickness — 8 mm. ix. Apex — Rounded. x. Base — Truncate. xi. Color — PMS 468. xii. Texture — Slightly grooved. xiii. Mucron — Present. xiv. Suture — Present. xv. Sides — Round. xvi. Ridges — Absent. xvii. Tendency to split — None.

DEVELOPMENT

General:

pp. *Flowering season*.—1-10 days during April.

qq. *Harvesting season*.—7 months from flowering to harvest.

rr. *Time to produce a fruit bearing tree*.—3 years.

ss. *Chilling requirements*.—Average/typical for olives.

tt. *Hardiness*.—Preferably adapted between 30 and 45 degrees on the north and south meridians (general in olive). 2023 USDA Plant Hardiness Zone Map: 8a-11b.

uu. *Plant/fruit disease resistance*.—i. *Verticillium* (*Verticillium dahlia*) — Moderately Resistant. ii. Tuberculosis (*Pseudomonas savastanoi*) — Moderately Resistant. iii. Olive Leaf Spot (*Spilocaea oleagina*) — Moderately Resistant.

vv. *Fruit market use*.—The new variety provides an oil with intense fruitiness and apple-green color. It has aromas of banana, apple and hints of almond shells. It is sweet and balanced on the palate, slightly bitter and slightly spicier.

ww. *Fruit yield*.—5-15 kg/tree and 8,000-20,000 kg/ha.

The new variety 'I 24' has not been observed under all possible environmental conditions to date. Accordingly, it is possible that the phenotypic expression may vary somewhat with changes in light intensity and duration, cultural practices, and other environmental conditions.

The invention claimed is:

1. A new and distinct variety of olive tree named 'I 24', as illustrated and described herein.

* * * * *